(12) United States Patent
Tanaka

(10) Patent No.: US 8,013,171 B2
(45) Date of Patent: Sep. 6, 2011

(54) AXIALLY ASYMMETRIC ESTER COMPOUND AND PRODUCTION METHOD THEREOF

(75) Inventor: Ken Tanaka, Fuchu (JP)

(73) Assignees: National University Corporation Tokyo University of Agriculture and Technology, Tokyo (JP); Takasago International Corporation, Tokyo (JP)

( * ) Notice: Subject to any disclaimer, the term of this patent is extended or adjusted under 35 U.S.C. 154(b) by 0 days.

(21) Appl. No.: 12/457,084

(22) Filed: Jun. 1, 2009

(65) Prior Publication Data

US 2009/0299076 A1    Dec. 3, 2009

(30) Foreign Application Priority Data

Jun. 2, 2008   (JP) ................................. 2008-144283
May 14, 2009  (JP) ................................. 2009-117750

(51) Int. Cl.
*C07C 69/78* (2006.01)
*C07D 209/44* (2006.01)
*C07D 307/87* (2006.01)
*C07D 333/72* (2006.01)

(52) U.S. Cl. ............ 548/470; 549/58; 549/462; 560/76; 560/102

(58) Field of Classification Search ................... 548/470; 549/58, 462
See application file for complete search history.

(56) References Cited

OTHER PUBLICATIONS

Nishida, et al. Organic Letters (2008) 10 2849-2852.*
Jesus A. Varela, et al., "Regiocontrolled One-Step Synthesis of 3,3'-Disubstituted 2,2'-Bipyridine Ligands by Cobalt(I)-Catalyzed Cyclotrimerization," Chem. Eur. J., 2001, pp. 5203-5213, vol. 7, No. 23.
Goushi Nishida, et al., "Enantioselective Synthesis of Tetra-*ortho*-Substituted Axially Chiral Biaryls through Rhodium-Catalyzed Double [2+2+2] Cycloaddition," Organic Letters, 2006, pp. 3489-3492, vol. 8, No. 16.
Takuya Hashimoto, et al., "Design of Axially Chiral Dicarboxylic Acid for Asymmetric Mannich Reaction of Arylaldehyde N-*Boc* Imines and Diazo Compounds," J. Am. Chem. Soc., 2007, pp. 10054-10055, vol. 129.

* cited by examiner

*Primary Examiner* — Shawquia Young
(74) *Attorney, Agent, or Firm* — Sughrue Mion, PLLC

(57) ABSTRACT

To provide an axially asymmetric optically active biaryl ester compound that can easily produced without the step of optical resolution which was almost indispensable in conventional methods. There is provided a method for producing an axially asymmetric ester compound, comprising a cycloaddition of a compound having a triple bond with the use of a catalyst containing rhodium metal and an optically active bisphosphine.

2 Claims, No Drawings

US 8,013,171 B2

AXIALLY ASYMMETRIC ESTER COMPOUND AND PRODUCTION METHOD THEREOF

TECHNICAL FIELD

The present invention relates to an axially asymmetric ester compound and a production method thereof.

BACKGROUND ART

Until now, optically active carboxylic acids have been applied to optical resolution of racemate, and determination of absolute configuration and enantiomeric excess. Furthermore, because of ease to handle and purchase, some optically active carboxylic acids have been used for an asymmetric ligand and a precursor thereof. Recently, several reports have been published on optically active carboxylic acids usable as a high performance organic catalyst (for example, Asymmetric Mannich Reaction; J. Am Chem. Soc., 2007, 129, 10054). Such optically active carboxylic acids as the usable organic catalyst have been widely known that they have an optically active biaryl structure. Many of the processes to synthesize such an optically active biaryl carboxylic acid derivative involve homo- or cross-coupling of two aryl units, and require optical resolution to obtain an optically active substance after the coupling. Recently, as a new technique for synthesizing a biaryl ester, usable as a precursor of carboxylic acid, a technique involving a [2+2+2] cycloaddition using alkynes has also been developed (Chem. Eur. J., 2001, Vol. 7, 5203-5213). Furthermore, a technique for producing an optically active biaryl ester compound involving an enantio-selective [2+2+2] cycloaddition has also been developed (Organic Letters, 2006, Vol. 8, 3489-3492).

SUMMARY OF THE INVENTION

Technical Problem

As described above, although the synthesis of a biaryl diester compound having an axially asymmetric structure by way of an enantio-selective [2+2+2] cycloaddition has been known, in view of a positional selectivity of a functional group, a chemical yield, an optical purity, and a narrow scope of applicable substrate, previous method have the issue.

Furthermore, it is indispensable to carry out optical resolution for a biaryl diester compound synthesized by a conventional coupling method of aryl units and in some cases, one optical isomer may be unnecessary.

In this context, if it is possible to synthesize an axially asymmetric biaryl ester compound in high optical purity from a substrate relatively easy to obtain through a reduced number of steps, an axially asymmetric optically active substance can easily be obtained without the step of optical resolution, which is almost indispensable step in a conventional method. The objective of the present invention is to provide such a production method and an axially asymmetric biaryl ester compound to be produced in such a manner.

Solution to Problem

As a result of keen examination to solve the problems, the inventors have found that an axially asymmetric biaryl ester compound having high optical purity can be produced in one step by an enantio-selective [2+2+2] cycloaddition reaction of a compound having a triple bond in the presence of a catalyst containing rhodium and an optically active bisphosphine, and have completed the present invention.

The present invention includes:

[1]. a method for producing an axially asymmetric ester compound represented by the following general formula (1):

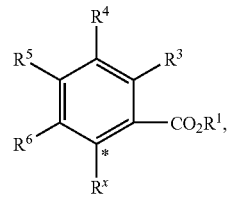

(1)

which comprises a cycloaddition of a compound having a triple bond with the use of a catalyst containing rhodium metal and an optically active bisphosphine (where, in the formula (1), $R^1$ is a hydrogen atom, alkali metal, or an alkyl group optionally having a substituent; $R^3$, $R^4$, $R^5$ and $R^6$ are independently a hydrogen atom, an alkyl group optionally having a substituent, a cycloalkyl group optionally having a substituent, an aryl group optionally having a substituent, an alkoxy group optionally having a substituent or an aryloxy group optionally having a substituent; any two adjacent groups among $R^3$ to $R^5$ may form a ring or a divalent group; $R^x$ is a group represented by the following formula ($R^x$); and * is axial asymmetry);

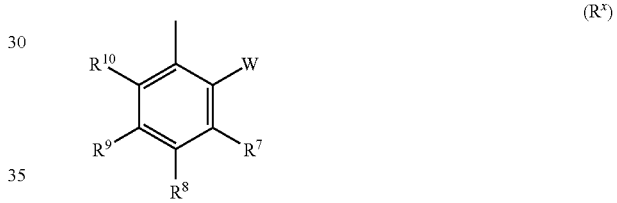

($R^x$)

(where, in the formula ($R^x$), $R^7$, $R^8$, $R^9$ and $R^{10}$ are independently a hydrogen atom, an alkyl group optionally having a substituent, a cycloalkyl group optionally having a substituent, an aryl group optionally having a substituent, an alkoxy group optionally having a substituent or an aryloxy group optionally having a substituent; W is $CO_2R^2$ or $OR^M$, $R^2$ is s hydrogen atom, alkali metal, or an alkyl group optionally having a substituent; $R^M$ is a hydrogen atom or a protecting group of hydroxyl group; and any two adjacent groups among $R^7$, $R^8$ and $R^9$ may form a ring or a divalent group, or $R^6$ and $R^{10}$ may form a ring or a divalent group);

[2]. the method according to the above mentioned [1], an axially asymmetric ester compound represented by the following general formula (4):

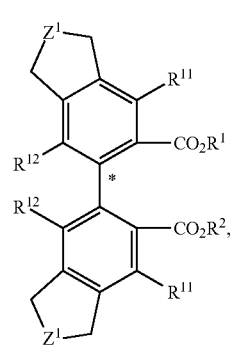

(4)

(where, in the formula (4), $R^1$ and $R^2$ are independently a hydrogen atom, alkali metal, or an alkyl group optionally having a substituent; $R^{11}$ and $R^{12}$ are independently a hydrogen atom, an alkyl group optionally having a substituent, a cycloalkyl group optionally having a substituent or an aryl group optionally having a substituent; $Z^1$ is a divalent group; and * is axial asymmetry;

which comprises an intermolecular cycloaddition of a diyne compound represented by the following general formula (2-1) and a diyne compound represented by the following general formula (3-1):

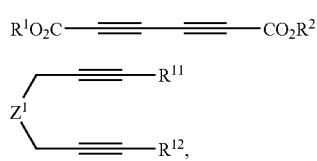

(2-1)

(3-1)

with the use of a catalyst containing rhodium metal and an optically active bisphosphine (where, in the formula (2-1), $R^1$ and $R^2$ are independently a hydrogen atom, alkali metal, or an alkyl group optionally having a substituent; and in the formula (3-1), $Z^1$ is a divalent group; and $R^{11}$ and $R^{12}$ are independently a hydrogen atom, an alkyl group optionally having a substituent, a cycloalkyl group optionally having a substituent or an aryl group optionally having a substituent);

[3]. the method according to the above mentioned [1], an axially asymmetric ester compound represented by the following general formula (5);

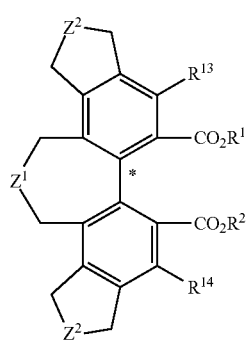

(5)

(where, in the formula (5), $R^1$ and $R^2$ are independently a hydrogen atom, alkali metal, or an alkyl group optionally having a substituent; $R^{13}$ and $R^{14}$ are independently a hydrogen atom, an alkyl group optionally having a substituent, a cycloalkyl group optionally having a substituent or an aryl group optionally having a substituent; $Z^1$ and $Z^2$ are a divalent group; and * is axial asymmetry), which comprises an intermolecular cycloaddition of a diyne compound represented by the following general formula (2-1) and a compound represented by the following general formula (3-2)

(2-1)

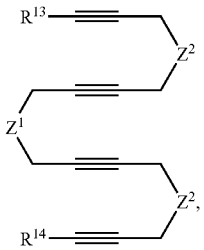

(3-2)

with the use of a catalyst containing rhodium metal and an optically active bisphosphine, (where, in the formula (2-1), $R^1$ and $R^2$ are independently a hydrogen atom, alkali metal, or an alkyl group optionally having a substituent; and in the formula (3-2), $Z^1$ and $Z^2$ are a divalent group; and $R^{13}$ and $R^{14}$ are independently a hydrogen atom, an alkyl group optionally having a substituent, a cycloalkyl group optionally having a substituent or an aryl group optionally having a substituent);

[4]. the method according to the above-mentioned [1], an axially asymmetric ester compound represented by the following general formula (8):

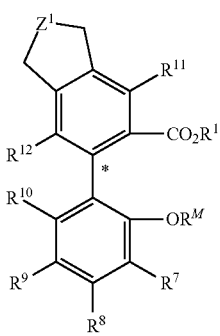

(8)

(where, in the formula (8), $R^1$ is s hydrogen atom, alkali metal, or an alkyl group optionally having a substituent; $R^M$ is a hydrogen atom or a protecting group of hydroxyl group; $R^7$, $R^8$, $R^9$ and $R^{10}$ are independently a hydrogen atom, an alkyl group optionally having a substituent, a cycloalkyl group optionally having a substituent, an aryl group optionally having a substituent, an alkoxy group optionally having a substituent or an aryloxy group optionally having a substituent; any two adjacent groups among $R^7$, $R^8$ and $R^9$ may form a ring or a divalent group; and $R^{11}$ and $R^{12}$ are independently a hydrogen atom, an alkyl group optionally having a substituent, a cycloalkyl group optionally having a substituent or an aryl group optionally having a substituent; $Z^1$ is a divalent group; and * is axial asymmetry), which comprises an intermolecular cycloaddition of a compound represented by the following general formula (2-2) and a diyne compound represented by the following general formula (3-1):

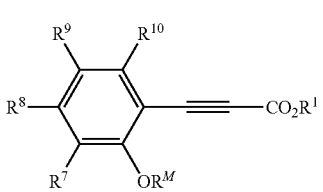

(2-2)

with the use of a catalyst containing rhodium metal and an optically active bisphosphine
(where, in the formula (2-2), $R^1$ is s hydrogen atom, alkali metal, or an alkyl group optionally having a substituent; $R^M$ is a hydrogen atom or a protecting group of hydroxyl group; $R^7$, $R^8$, $R^9$ and $R^{10}$ are the same or different and are each independently a hydrogen atom, an alkyl group optionally having a substituent, a cycloalkyl group optionally having a substituent, an aryl group optionally having a substituent, an alkoxy group optionally having a substituent or an aryloxy group optionally having a substituent; and any two adjacent groups among $R^7$, $R^8$ and $R^9$ may form a ring or a divalent group; and in the formula (3-1), $R^{11}$ and $R^{12}$ are independently a hydrogen atom, an alkyl group optionally having a substituent, a cycloalkyl group optionally having a substituent or an aryl group optionally having a substituent; $Z^1$ is a divalent group);

[5]. the method according to any one of the above-mentioned [1] to [4], wherein the catalyst containing rhodium metal and an optically active bisphosphine is a compound represented by the following general formula (6):

$$[Rh(L)_m(Y)_n]X \quad (6)$$

(where, in the formula (6), L is an optically active bisphosphine represented by the following formula (7); Y is a non-conjugated diene compound; X is a counter anion; m is an integer 1 or 2; n is an integer 0 or 1; when m is 1, n is 0 or n is 1; and when m is 2, n is 0);

$$R^{15}R^{16}P-Q-PR^{17}R^{18} \quad (7)$$

(where, in the formula (7), $R^{15}$, $R^{16}$, $R^{17}$, and $R^{18}$ are independently an aryl group optionally having a substituent, a cycloalkyl group optionally having a substituent or an alkyl group optionally having a substituent; $R^{15}$ in combination with $R^{16}$ and/or $R^{17}$ in combination with $R^{18}$ may form a ring; and Q is a divalent arylene group optionally having a substituent or a ferrocenediyl group optionally having a substituent);

[6]. the method according to the above-mentioned [5], wherein a olefinic ligand is eliminated with the use of hydrogen gas in preparing the catalyst containing rhodium metal and an optically active bisphosphine;

[7]. an optically active compound represented by the following general formula (4'):

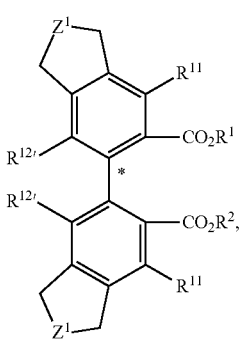

(where, in the formula (4'), $R^1$ and $R^2$ maybe the same or different and are a hydrogen atom, alkali metal, or an alkyl group optionally having a substituent; $R^{11}$ is hydrogen atom, an alkyl group optionally having a substituent, a cycloalkyl group optionally having a substituent or an aryl group optionally having a substituent; $R^{12'}$ is an alkyl group optionally having a substituent, a cycloalkyl group optionally having a substituent or an aryl group optionally having a substituent; $Z^1$ is a divalent group; two $R^{12'}$ may form a ring or a divalent group in combination with each other; and * is axial asymmetry); and

[8]. an optically active compound represented by the following general formula (8'):

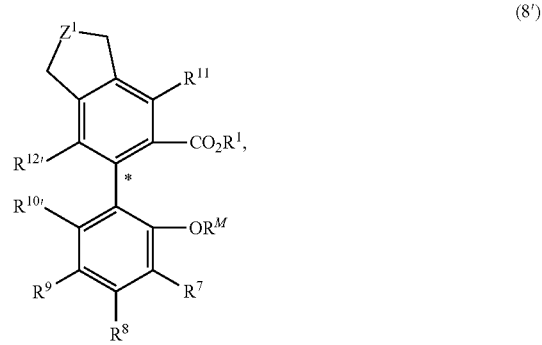

(where, in the formula (8'), $R^1$ is a hydrogen atom, alkali metal, or an alkyl group optionally having a substituent; $R^M$ is a hydrogen atom or a protecting group of hydroxyl group; $R^7$, $R^8$ and $R^9$ are independently a hydrogen atom, an alkyl group optionally having a substituent, a cycloalkyl group optionally having a substituent, an aryl group optionally having a substituent, an alkoxy group optionally having a substituent or an aryloxy group optionally having a substituent; $R^{11}$ is a hydrogen atom, an alkyl group optionally having a substituent, a cycloalkyl group optionally having a substituent or an aryl group optionally having a substituent; $R^{10'}$ and $R^{12'}$ are independently, an alkyl group optionally having a substituent, a cycloalkyl group optionally having a substituent or an aryl group optionally having a substituent; any two adjacent groups among $R^7$, $R^8$ and $R^9$ may form an aromatic ring optionally having a substituent, a methylene chain optionally having a substituent or a (poly)methylenedioxy group optionally having a substituent; $Z^1$ is a divalent group; and * is axial asymmetry)

Advantageous Effects of Invention

According to the process of the invention, since it is possible to enantio-selectively produce an optically active biaryl ester compound in one step by reacting a compound having a plurality of triple bonds and an ester compound having a yne structure in the presence of a catalyst containing rhodium metal and an optically active bisphosphine, an axially asymmetric optically active substance can be obtained without the step of optical resolution. Furthermore, an optically active biaryl ester compound within the scope of the invention can easily be produced with the use of a substrate relatively easy to obtain and is useful as an intermediate of a metal catalyst's ligand, or of an asymmetric organic catalyst.

DESCRIPTION OF EMBODIMENTS

Hereinafter, the invention will be described in more detail.

An ester compound of the invention is an ester compound represented by the above-mentioned general formula (1), (4), (5), (8), (4') or (8'), and can be produced by the production method of the invention, which will be described in detail below. In the general formulas (1), (4), (5), (8), (4') and (8'), $R^1$ and $R^2$ are the same or different and are each independently are a hydrogen atom, an alkali metal or an alkyl group optionally having a substituent.

Herein, the alkyl group represented by $R^1$ or $R^2$ may be, for example, a linear or branched alkyl group having 1 to 15 carbon atoms, preferably 1 to 10 carbon atoms, more preferably 1 to 6 carbon atoms. Specific examples include, for example, a methyl, ethyl, n-propyl, isopropyl, n-butyl, s-butyl, isobutyl, t-butyl, pentyl, and hexyl group. These alkyl groups may have a substituent, and the examples of the substituent include, for example, an alkoxy group and a halogen atom.

In the general formulas (1), (4), (5) (8), (4') and (8'), $R^3$ to $R^{10}$ represent a hydrogen atom, an alkyl group optionally having a substituent, a cycloalkyl group optionally having a substituent, an aryl group optionally having a substituent, an alkoxy group optionally having a substituent or an aryloxy group optionally having a substituent; and $R^{11}$ to $R^{14}$, $R^{10'}$ and $R^{12'}$ represent a hydrogen atom, an alkyl group optionally having a substituent, a cycloalkyl group optionally having a substituent or an aryl group optionally having a substituent. The alkyl group represented by $R^3$ to $R^{14}$, $R^{10'}$ and $R^{12'}$ may be, for example, a linear or branched alkyl group having 1 to 15 carbon atoms, preferably 1 to 10 carbon atoms, more preferably 1 to 6 carbon atoms. Specific examples include, for example, a methyl, ethyl, n-propyl, isopropyl, n-butyl, s-butyl, isobutyl, t-butyl, pentyl, and hexyl group. These alkyl groups may have a substituent, and the examples of the substituent include, for example, an alkoxy group and a halogen atom.

The cycloalkyl group represented by $R^3$ to $R^{14}$, $R^{10'}$ and $R^{12'}$ may be a cycloalkyl group having 3 to 12 carbon atoms, and specific examples include, for example, a cyclopropyl, cyclobutyl, cyclopentyl, cyclohexyl, cycloheptyl, cyclooctyl, and adamantyl group. These cycloalkyl groups may have a substituent, and the examples of the substituent include, for example, an alkoxy group and a halogen atom.

The aryl group represented by $R^3$ to $R^{14}$, $R^{10'}$ and $R^{12'}$ may be an aryl group having 6 to 18 carbon atoms, and specific examples include a phenyl, naphthyl, anthryl, phenanthryl, and biphenyl group. These aryl groups may have a substituent and examples of the substituent include, for example, linear or branched alkyl groups having 1 to 6 carbon atoms such as methyl and t-butyl; linear or branched alkoxy groups having 1 to 6 carbon atoms such as methoxy and t-butoxy; and halogen atoms such as chlorine, bromine, and fluorine; and a plurality of these substituents may be introduced into the aryl groups.

The alkoxy group represented by $R^3$ to $R^{10}$ may be, a linear or branched alkoxy group, for example, having 1 to 15 carbon atoms, preferably 1 to 10 carbon atoms, and more preferably 1 to 6 carbon atoms. Specific examples include, for example, a methoxy, ethoxy, n-propoxy, isopropoxy, n-butoxy, s-butoxy, isobutoxy, t-butoxy, pentyloxy, and hexyloxy group. These alkoxy groups may have a substituent, and the examples of the substituent include, for example, a halogen atom and an aryl group.

The aryloxy group represented by $R^3$ to $R^{10}$ may be an aryloxy group having 6 to 18 carbon atoms, and specific examples are phenyloxy, naphthyloxy, anthryloxy, phenanthryloxy, and biphenyloxy. These aryloxy groups may have a substituent and examples of the substituent include, for example, linear or branched alkyl groups having 1 to 6 carbon atoms such as methyl and t-butyl; linear or branched alkoxy groups having 1 to 6 carbon atoms such as methoxy and t-butoxy; and halogen atoms such as chlorine, bromine, and fluorine, and a plurality of these substituents may be introduced into the aryl group.

Any two adjacent groups selected from $R^3$, $R^4$ and $R^5$ and any two adjacent groups selected from $R^7$, $R^8$ and $R^9$ in the general formula (1), two $R^{12}$ in the general formula (4), two $R^{12'}$ in the general formula (4'), any two adjacent groups selected from $R^7$, $R^8$ and $R^9$ in the general formula (8), and any two adjacent groups selected from $R^7$, $R^8$ and $R^9$ and $R^{10'}$ and $R^{12'}$ in the general formula (8') may form a ring or a divalent group.

Specific examples of the ring to be formed include aliphatic rings such as cyclobutane, cyclopentane and cyclohexane; and aromatic rings such as benzene, naphthalene, anthracene, and phenanthrene. The examples of the substituent on the ring include an alkyl group, an alkoxy group and a halogen atom, and specific examples of these groups include, for example, the above-mentioned groups.

The divalent group to be formed may be a methylene chain optionally having a substituent and optionally having a heteroatom such as an oxygen atom and a sulfur atom in the chain. The methylene chain in such a case may be, for example, preferably a methylene chain having 3 to 6 carbon atoms, and specific examples of the methylene chain are trimethylene, tetramethylene, pentamethylene, and hexamethylene. A carbon atom in the above-mentioned methylene chain may be replaced by a heteroatom such as an oxygen atom, an nitrogen atom and a sulfur atom, and specific example of such a group include 2-oxatrimethylene, 3-oxapentamethylene, methylenedioxy, and 2,4-dioxapentamethylene group. The examples of the substituent on the methylene chain include an alkyl group having 1 to 4 carbon atoms, an alkoxy group having 1 to 4 carbon atoms, an alkoxycarbonyl group having an alkoxy group of 1 to 4 carbon atoms, and a halogen atom.

In the general formula ($R^x$), (8) and (8'), the protecting group of hydroxyl group represented by $R^M$ is, for example, an alkyl group, an aralkyl group, an acyl group, and a trisubstituted silyl group.

Herein, the alkyl group represented by $R^M$ may be a linear or branched alkyl group, for example, having 1 to 15 carbon atoms, preferably 1 to 10 carbon atoms, and more preferably 1 to 6 carbon atoms. Specific examples of the alkyl group include, for example, a methyl, ethyl, n-propyl, isopropyl, n-butyl, s-butyl, isobutyl, t-butyl, pentyl, and hexyl group. These alkyl groups may have a substituent selected from an alkoxy group, and specific example of the alkoxy alkyl group is a methoxymethyl, ethoxymethyl, t-butoxymethyl, and 2-methoxyethoxymethyl group.

The aralkyl group represented by $R^M$ is, for example, a benzyl, p-methoxybenzyl, 1-phenylmethyl, and triphenylmethyl group.

The acyl group represented by $R^M$ may be a linear or branched aliphatic acyl group having 1 to 10 carbon atoms and aromatic acyl group. Specific examples of the acyl group include, for example, an acetyl, propanoyl, butyryl, pivaloyl, methoxycarbonyl, ethoxycarbonyl, benzyloxycarbonyl, benzoyl, and p-nitrobenzoyl group.

The trisubstituted silyl group represented by $R^M$ is, for example, a trimethylsilyl, triethylsilyl, triisopropylsilyl, and t-butyldimethylsilyl group.

The divalent group denoted by $Z^1$ and $Z^2$ in the formulas (3-1), (3-2), (4), (5), (8), (4') and (8') may include, for example, an oxygen atom, a sulfur atom, a methylene chain, $NR^N$, and $Si(R^{Si})_2$. Herein, $R^N$ is an alkyl, aryl, alkanesulfonyl, arylsulfonyl, or acyl group, and $R^{Si}$ is an alkyl or aryl group or may form a ring as $Si(R^{Si})_2$.

The methylene chain may include, for example, a linear or branched methylene chain and examples of the methylene chain are a methylene, ethylene, trimethylene, propylene, isopropylidene, 2,3-butanediyl, and difluoromethylene group.

The alkyl group denoted by $R^N$ of $NR^N$ and $R^{Si}$ of $Si(R^{Si})_2$ may include, for example, linear or branched alkyl groups having 1 to 6 carbon atoms, and specific examples of the alkyl group are the above-mentioned alkyl groups. The aryl group represented by $R^N$ or $R^{Si}$ may include aryl groups having 6 to 18 carbon atoms, and specific examples of the aryl group are the above-mentioned aryl groups.

The alkanesulfonyl and arylsulfonyl group represented by $R^N$ of $NR^N$ may include, for example, a methanesulfonyl, trifluoromethanesulfonyl, benzenesulfonyl, and p-toluenesulfonyl group.

The acyl group represented by $R^N$ may include, for example, linear or branched aliphatic acyl groups having 2 to 10 carbon atoms and aromatic acyl groups, and specific examples of the acyl group may include an acetyl, propanoyl, butyryl, pivaloyl, methoxycarbonyl, ethoxycarbonyl, t-butoxycarbonyl, benzyloxycarbonyl, benzoyl, and p-nitrobenzoyl group.

The ring formed as $Si(R^{Si})_2$ maybe a silolane ring, a silinane ring, or a silepane ring.

In the invention, the ester compounds represented by the general formula (1) are preferably the ester compounds represented by the general formulas (4), (8), (4') and (8').

Next, a method for producing an axially asymmetric optically active ester compound, which can be used for producing the ester compound of the invention (referred to simply as the production method of the invention in some cases), will be described.

As described in the following schemes 1 and 2, the production method of an axially asymmetric optically active ester compound of the invention causes a reaction in the presence of a catalyst containing rhodium metal and an optically active bisphosphine compound, and more particularly causes an enantio-selective [2+2+2] cycloaddition.

SCHEME 1

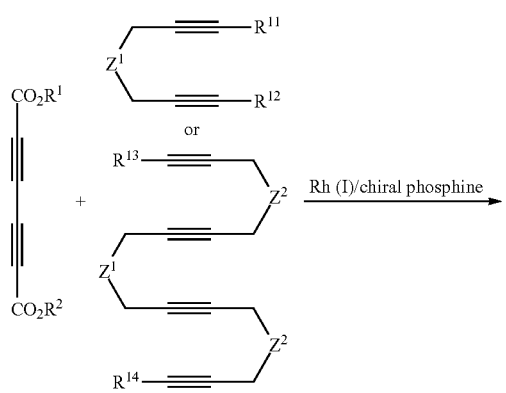

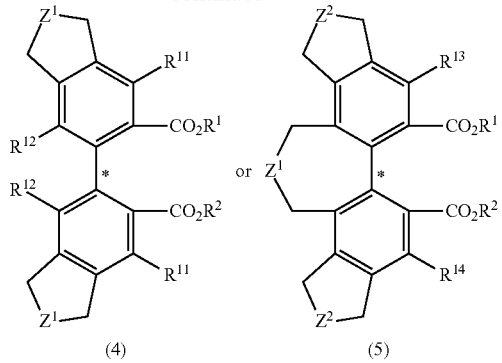

SCHEME 2

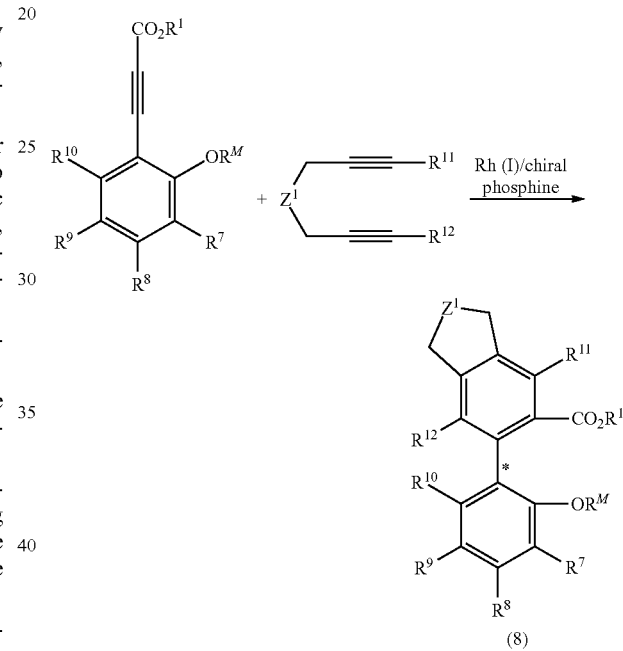

Definitions of the reference characters and examples of the groups represented by these reference characters described also in the schemes are the same as those described above.

The catalyst containing rhodium metal and an optically active bisphosphine compound used in the production method of the invention will be described.

As the rhodium source for the rhodium metal used as one component of the catalyst of the invention, rhodium compounds may be used, and preferable rhodium compounds may be complexes of rhodium(I) coordinated with an olefinic ligand. Specific examples of rhodium(I) complexes are [Rh(COD)$_2$]X, [Rh(NBD)$_2$]X, [Rh(ethylene)$_2$Cl]$_2$, [Rh(COE)$_2$Cl]$_2$, [Rh(COD)Cl]$_2$, and [Rh(NBD)Cl]$_2$. In the above-mentioned chemical formulas of the complexes, X is a counter anion such as Cl, Br, I, $BF_4$, OTf, $ClO_4$, $SbF_6$, $PF_6$, $BPh_4$, and $B((3,5-CF_3)_2C_6H_3)_4)$; COE is cyclooctene; COD is 1,5-cyclooctadiene; and NBD is norbornadiene.

Examples of the optically active bisphosphine compound that is the other catalytic component used for the invention are those represented by the following general formula (7):

$$R^{15}R^{16}P\text{-}Q\text{-}PR^{17}R^{18} \qquad (7)$$

(where, in the formula (7), $R^{15}$, $R^{16}$, $R^{17}$, and $R^{18}$ independently are an aryl group optionally having a substituent, a cycloalkyl group optionally having a substituent or an alkyl group optionally having a substituent; $R^{15}$ in combination with $R^{16}$ and/or $R^{17}$ in combination with $R^{18}$ may form a ring; and Q is a divalent arylene group optionally having a substituent or a ferrocenediyl group optionally having a substituent).

In the above formula, the aryl group optionally having a substituent denoted by $R^{15}$, $R^{16}$, $R^{17}$, or $R^{18}$ may be an aryl group having 6 to 14 carbon atoms, and specific examples of the aryl group are phenyl, naphthyl, anthryl, phenanthryl, and biphenyl. These aryl groups may have a substituent, and the substituent may be an alkyl, alkoxy, aryl, and heterocyclic group.

The alkyl group as a substituent of the aryl group may include, for example, linear or branched alkyl groups having 1 to 15 carbon atoms, preferably 1 to 10 carbon atoms, and more preferably 1 to 6 carbon atoms, and specific examples of the alkyl group are a methyl, ethyl, n-propyl, isopropyl, n-butyl, s-butyl, isobutyl and t-butyl group.

The alkoxy group as a substituent of the aryl group may include, for example, linear or branched alkoxy groups having 1 to 6 carbon atoms, and specific examples of the alkoxy group are a methoxy, ethoxy, n-propoxy, isopropoxy, n-butoxy, s-butoxy, isobutoxy and t-butoxy group.

The aryl group as a substituent of the aryl group may include, for example, aryl groups having 6 to 14 carbon atoms, and specific examples of the aryl group are phenyl, naphthyl, anthryl, phenanthryl, and biphenyl.

The heterocyclic group as a substituent of the aryl group may include, for example, aliphatic heterocyclic groups and aromatic heterocyclic groups. The aliphatic heterocyclic groups may include, for example, 5- to 8-membered and preferably 5- or 6-membered mono-cyclic, polycyclic, and condensed aliphatic hetero rings having 2 to 14 carbon atoms and at least one, preferably 1 to 3 heteroatoms such as nitrogen, oxygen, and sulfur atoms. Specific examples of the aliphatic heterocyclic groups are, for example, a 2-oxopyrrolidyl, piperidino, piperadinyl, morpholino, tetrahydrofuryl, tetrahydropyranyl, and tetrahydrothienyl group. On the other hand, the aromatic heterocyclic groups may include, for example, 5- to 8-membered and preferably 5- or 6-membered mono-cyclic, polycyclic, and condensed cyclic heteroaryl groups having 2 to 15 carbon atoms and at least one, preferably 1 to 3 heteroatoms such as nitrogen, oxygen, and sulfur atoms. Specific examples of the aromatic heterocyclic groups are a furyl, thienyl, pyridyl, pyrimidinyl, pyradinyl, pyridadinyl, pyrazolyl, imidazolyl, oxazolyl, thiazolyl, benzofuryl, benzothienyl, quinolyl, isoquinolyl, quinoxalyl, phthalazinyl, quinazolinyl, naphthyldinyl, cinnolinyl, benzoimidazolyl, benzoxazolyl, and benzothiazolyl group.

The cycloalkyl optionally having a substituent denoted by $R^{15}$, $R^{16}$, $R^{17}$, or $R^{18}$ may be a 5- or 6-membered cycloalkyl group, and preferable cycloalkyl groups are a cyclopentyl and cyclohexyl group. These cycloalkyl groups may have one or more alkyl or alkoxy substituents as exemplified above for the aryl group on the ring.

The alkyl group optionally having a substituent denoted by $R^{15}$, $R^{16}$, $R^{17}$, or $R^{18}$ may be, for example, a linear or branched alkyl group having 1 to 15 carbon atoms, preferably 1 to 10 carbon atoms, more preferably 1 to 6 carbon atoms. Specific examples of the alkyl group include, for example, a methyl, ethyl, n-propyl, isopropyl, n-butyl, s-butyl, isobutyl, t-butyl, pentyl, and hexyl group. These alkyl groups may have a substituent, and the examples of the substituent include, for example, an alkoxy group and a halogen atom.

Furthermore, the ring formed by combination of $R^{15}$ with $R^{16}$ and/or $R^{17}$ with $R^{18}$ maybe a 4-, 5-, or 6-membered ring containing a phosphorus atom to which $R^{15}$, $R^{16}$, $R^{17}$, and $R^{18}$ are bound. Specific examples of the ring are a phosphetane, phospholane, phosphane, 2,4-dimethylphosphetane, 2,4-diethylphosphetane, 2,5-dimethylphospholane, 2,5-diethylphospholane, 2,6-dimethylphosphane, and 2,6-diethylphosphane ring. These rings may be optically active substances.

The divalent arylene optionally having a substituent denoted by Q may be a phenylene, biphenyldiyl, and binaphthalenediyl group. The phenylene group includes, for example, an o- or m-phenylene group, and may have a substituent selected from an alkyl group such as a methyl, ethyl, n-propyl, isopropyl, n-butyl, s-butyl, isobutyl, and t-butyl group; an alkoxy group such as a methoxy, ethoxy, n-propoxy, isopropoxy, n-butoxy, s-butoxy, isobutoxy, and t-butoxy group; a hydroxyl group; an amino group; and a substituted amino group. The biphenyldiyl group and the binaphthalenediyl group preferably have a 1,1'-biaryl-2,2'-diyl type structure, and may have a substituent selected from the above-mentioned alkyl group and alkoxy group; an alkylenedioxy group such as a methylenedioxy, ethylenedioxy, and trimethylenedioxy group; a hydroxyl group; an amino group; and a substituted amino group. Furthermore, the ferrocenediyl group also may have a substituent, and the substituent may be, for example, the above-mentioned alkyl group, alkoxy group, alkylenedioxy group, hydroxyl group, amino group, and substituted amino group.

Specific examples of the optically active bisphosphine compound represented by the general formula (7) may be a conventionally known bisphosphine, and one example of the bisposphine is a compound represented by the following general formula (9).

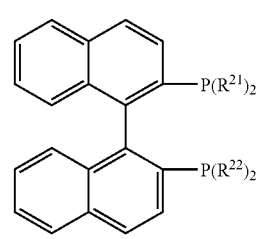

(9)

(In the formula (9), $R^{21}$ and $R^{22}$ independently are a phenyl group optionally having a substituent selected from a halogen atom, an alkyl group, and an alkoxy group, or are a cyclopentyl group or a cyclohexyl group.)

In the above $R^{21}$ and $R^{22}$, the alkyl group as a substituent of the phenyl may include, for example, linear or branched alkyl groups having 1 to 6 carbon atoms such as a methyl and t-butyl group; the alkoxy group as a substituent of the phenyl may include, for example, linear or branched alkoxy groups having 1 to 6 carbon atoms such as a methoxy and t-butoxy group; and the halogen atom as a substituent of the phenyl may include, for example, a chlorine, bromine, and fluorine atom. A plurality of these substituents may be introduced into the phenyl group.

Specific examples of $R^{21}$ and $R^{22}$ are a phenyl, p-tolyl, m-tolyl, o-tolyl, 3,5-xylyl, 3,5-di-t-butylphenyl, p-t-butylphenyl, p-methoxyphenyl, 3,5-di-t-butyl-4-methoxyphenyl, p-chlorophenyl, m-chlorophenyl, p-fluorophenyl, m-fluorophenyl, cyclopentyl, and cyclohexyl group.

The binaphthyl ring that is the basic skeleton of the compound represented by the general formula (9) may have a substituent, and the substituent may include, for example, alkyl groups such as a methyl and t-butyl group; alkoxy groups such as a methoxy and t-butoxy group; trialkylsilyl groups such as a trimethylsilyl, triisopropylsilyl, and t-butyldimethylsilyl group; and triarylsilyl groups such as a triphenylsilyl group.

Another specific example of the optically active bisphosphine compound represented by the general formula (7) may be a compound represented by the following general formula (10).

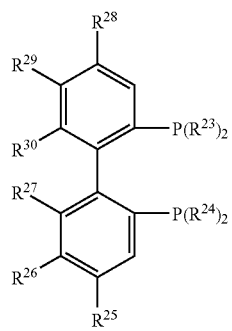

(10)

(In the formula (10), $R^{23}$ and $R^{24}$ independently are a phenyl group optionally having a substituent selected from a halogen atom, an alkyl group, and an alkoxy group, or are a cyclopentyl, or cyclohexyl group. $R^{25}$, $R^{26}$, $R^{28}$ and $R^{29}$ may be the same or different and independently are a hydrogen atom, an alkyl group, an alkoxy group, an acyloxy group, a halogen atom, a haloalkyl group, or a dialkylamino group; $R^{27}$ and $R^{30}$ may be the same or different and independently are an alkyl group, an alkoxy group, an acyloxy group, a halogen atom, a haloalkyl group, or a dialkylamino group; any two adjacent groups among $R^{25}$, $R^{26}$, and $R^{27}$ may form a methylene chain optionally having a substituent or a (poly)methylenedioxy group optionally having a substituent; any two adjacent groups among $R^{28}$, $R^{29}$, and $R^{30}$ may form a methylene chain optionally having a substituent or a (poly)methylenedioxy group optionally having a substituent; $R^{27}$ and $R^{30}$ may form a methylene chain optionally having a substituent or a (poly) methylenedioxy group optionally having a substituent.)

In the above $R^{23}$ and $R^{24}$, the alkyl group as a substituent of the phenyl may include, for example, linear or branched alkyl groups having 1 to 6 carbon atoms such as a methyl and t-butyl group; the alkoxy group as a substituent of the phenyl may include, for example, linear or branched alkoxy groups having 1 to 6 carbon atoms such as a methoxy and t-butoxy group; and the halogen atom as a substituent of the phenyl may include, for example, a chlorine, bromine, and fluorine atom. A plurality of these substituents may be introduced into the phenyl group. Specific examples of $R^{23}$ and $R^{24}$ are a phenyl, p-tolyl, m-tolyl, o-tolyl, 3,5-xylyl, 3,5-di-t-butylphenyl, p-t-butylphenyl, p-methoxyphenyl, 3,5-di-t-butyl-4-methoxyphenyl, p-chlorophenyl, m-chlorophenyl, p-fluorophenyl, m-fluorophenyl, cyclopentyl, and cyclohexyl group.

The alkyl group denoted by $R^{25}$ to $R^{30}$ may include, for example, linear or branched alkyl groups having 1 to 6 carbon atoms such as a methyl and t-butyl group; the alkoxy group denoted by $R^{25}$ to $R^{30}$ may include, for example, linear or branched alkoxy groups having 1 to 6 carbon atoms such as a methoxy and t-butoxy group; the acyloxy group denoted by $R^{25}$ to $R^{30}$ may include, for example, acyloxy groups having 2 to 10 carbon atoms such as an acetoxy, propanoyloxy, trifluoroacetoxy, and benzoyloxy group; the halogen atom denoted by $R^{25}$ to $R^{30}$ may include, for example, a chlorine, bromine, and fluorine atom; the haloalkyl group denoted by $R^{25}$ to $R^{30}$ may include, for example, haloalkyl groups having 1 to 4 carbon atoms such as a trifluoromethyl group; and the dialkylamino group denoted by $R^{25}$ to $R^{30}$ may include, for example, a dimethylamino and diethylamino group.

In the case where two of $R^{25}$, $R^{26}$, and $R^{27}$ form a methylene chain optionally having a substituent and in the case where two of $R^{28}$, $R^{29}$, and $R^{30}$ form a methylene chain optionally having a substituent, the methylene chain preferably includes, for example, methylene chains having 3 to 5 carbon atoms, and specific examples of the methylene chains are a trimethylene, tetramethylene, and pentamethylene group. The substituent in the methylene chain optionally having the substituent may be an alkyl group or a halogen atom, and specific examples of the substituent are the above-mentioned alkyl groups having 1 to 6 carbon atoms and a fluorine atom.

In the case where two of $R^{25}$, $R^{26}$, and $R^{27}$ form a (poly) methylenedioxy group optionally having a substituent and in the case where two of $R^{28}$, $R^{29}$, and $R^{30}$ form a (poly)methylenedioxy group optionally having a substituent, specific examples of the (poly)methylenedioxy group are a methylenedioxy, ethylenedioxy, and trimethylenedioxy group. The substituent in the (poly)methylenedioxy may be an alkyl group or a halogen atom, and specific examples of the substituent are the above-mentioned alkyl groups having 1 to 6 carbon atoms and a fluorine atom.

Specific examples of the optically active bisphosphine compound represented by the general formula (9) or (10) are, for example, 2,2'-bis(diphenylphosphino)-1,1'-binaphthyl, 2,2'-bis[di(p-tolyl)phosphino]-1,1'-binaphthyl, 2,2'-bis[di(m-tolyl)phosphino]-1,1'-binaphthyl, 2,2'-bis[di(3,5-xylyl)phosphino]-1,1'-binaphthyl, 2,2'-bis[di(p-t-butylphenyl)phosphino]-1,1'-binaphthyl, 2,2'-bis[di(p-methoxyphenyl)phosphino]-1,1'-binaphthyl, 2,2'-bis[di(3,5-di-t-butyl-4-methoxyphenyl)phosphino]-1,1'-binaphthyl, 2,2'-bis[di(cyclopentyl)phosphino]-1,1'-binaphthyl, 2,2'-bis[di(cyclohexyl)phosphino]-1,1'-binaphthyl, 2,2'-bis(diphenylphosphino)-5,5',6,6',7,7',8,8'-octahydro-1,1'-binaphthyl, 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di-3,5-xylylphosphino)-5,5',6,6',7,7',8,8'-octahydro-1,1'-binaphthyl, 2,2'-bis(di-p-t-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine) (hereinafter, referred to as segphos), ((4,4'-bi-1,3-benzodioxole)-5,5'-diyl)bis(di(3,5-dimethylphenyl)phosphine), ((4,4'-bi-1,3-benzodioxole)-5,5'-diyl)bis(di(3,5-di-t-butyl-4-methoxyphenyl)phosphine), ((4,4'-bi-1,3-benzodioxole)-5,5'-diyl)bis(di(4-methoxyphenyl)phosphine), ((4,4'-bi-1,3-benzodioxole)-5,5'-diyl)bis(dicyclohexylphosphine), ((4,4'-bi-1,3-benzodioxole)-5,5'-diyl)bis(bis(3,5-di-t-butylphenyl)phosphine), 2,2'-bis(diphenylphosphino)-4,4',6,6'-tetramethyl-5,5'-dimethoxy-1,1'-biphenyl, 2,2'-bis(di-p-methoxyphenylphosphino)-4,4',6,6'-tetramethyl-5,5'-dimethoxy-1,1'-biphenyl, 2,2'-bis (diphenylphosphino)-4,4',6,6'-tetra(trifluoromethyl)-5,5'-dimethyl-1,1'-biphenyl, 2,2'-bis(diphenylphosphino)-4,6-di(trifluoromethyl)-4',6'-dimethyl-5'-methoxy-1,1'-biphenyl, 2-dicyclohexylphosphino)-2'-diphenylphosphino-4,4',6,6'-tetramethyl-5,5'-dimethoxy-1,1'-biphenyl, 2,2'-bis(diphenylphosphino)-6,6'-dimethyl-1,1'-biphenyl, 2,2'-bis(diphenylphosphino)-4,4',6,6'-tetramethyl-1,1'-biphenyl), 2,2'-bis(diphenylphosphino)-3,3',6,6'-tetramethyl-1,1'-biphenyl, 2,2'-bis(diphenylphosphino)-4,4'-difluoro-6,6'-dimethyl-1,1'-biphenyl, 2,2'-bis(diphenylphosphino)-4,4'-bis(dimethylamino)-6,6'-dimethyl-1,1'-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 1,11-bis(diphenylphosphino)-5,7-dihydrobenzo[c,e]oxepine, 2,2'-bis(diphenylphosphino)-6,6'-dimethoxy-1,1'-biphenyl, 2,2'-bis(diphenylphosphino)-5,5',6,6'-tetramethoxy-1,1'-biphenyl, 2,2'-bis(di-p-tolylphosphino)-6,6'-dimethoxy-1,1'-biphenyl, 2,2'-bis(diphenylphosphino)-4,4',5,5',6,6'-hexamethoxy-1,1'-biphenyl, 1,2-bis(2,5-dimethylphospholano)benzene, 1,2-bis(2,5-diethylphospholano)benzene, 1,2-bis(2,5-diisopropylphospholano)benzene, 1-(2,5-dimethylphospholano)-2-(diphenylphosphino)benzene, and 1,1'-bis(2,4-diethylphosphotano)ferrocene.

Additionally, specific examples of the optically active bisphosphine compound used in the invention may also include, for example, N,N-dimethyl-1-[1',2-bis(diphenylphosphino)ferrocenyl]ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis[(o-methoxyphenyl)phenylphosphino]ethane, 1,2-bis(2,5-dimethylphospholano)ethane, 5,6-bis(diphenylphosphino)-2-norbornene, N,N-bis(diphenylphosphino)-N,N'-bis(1-phenylethyl)ethylenediamine, 1,2-bis(diphenylphosphino)propane, and 2,4-bis(diphenylphosphino)pentane.

The catalyst used in the invention is a catalyst containing rhodium metal and an optically active bisphosphine, as described above, as catalytic components, and is a compound represented by the following general formula (6).

$$[Rh(L)_m(Y)_n]X \quad (6)$$

(In the formula (6), L is an optically active bisphosphine represented by $R^{15}R^{16}P$-Q-$PR^{17}R^{18}$; Y is a nonconjugated diene compound; X is a counter anion; m is an integer 1 or 2; n is an integer 0 or 1; when m is 1, n is 0 or n is 1; when m is 2, n is 0. $R^{15}$, $R^{16}$, $R^{17}$, and $R^{18}$ independently are an aryl group optionally having a substituent, a cycloalkyl group optionally having a substituent or an alkyl group optionally having a substituent; $R^{15}$ in combination with $R^{16}$ and/or $R^{17}$ in combination with $R^{18}$ may form a ring; and Q is a divalent arylene group optionally having a substituent or a ferrocene-diyl group optionally having a substituent.)

The optically active bisphosphine denoted by L, that is $R^{15}R^{16}P$-Q-$PR^{17}R^{18}$, in the above formula, is as described above.

Next, the compound represented by the general formula (6) as an example of the catalyst containing rhodium metal and the optically active bisphosphine used in the invention will be described in more detail.

In the general formula (6), the non-conjugated diene compound denoted by Y may be cyclic or acyclic, and in the case where the non-conjugated diene compound is a cyclic non-conjugated diene compound, the compound may include monocyclic, polycyclic, condensed cyclic or bicyclo compounds. Furthermore, the non-conjugated diene compound may include, for example, a non-conjugated diene compound having a substituent, that is, a substituted non-conjugated diene compound, and the substituent is not particularly limited as long as it does not negatively affect the production method of the invention. Preferable non-conjugated diene compounds are, for example, 1,5-cyclooctadiene, bicyclo[2,2,1]hepta-2,5-diene, and 1,5-hexadiene.

In the general formula (6), the counter anion denoted by X include, for example, chloride ion, bromide ion, iodide ion, $BF_4$, $ClO_4$, $CF_3SO_3$ (hereafter abbreviated as OTf), $PF_6$, $SbF_6$, $B(3,5-(CF_3)_2C_6H_3)_4$, and $BPh_4$.

The compound represented by the general formula (6) used in the invention can be obtained, for example, by a conventionally known method as shown in the following scheme 3 under an inert gas atmosphere; or by counter-anion-exchange reaction with MX (M is a monovalent metal cation; and X is the same as described above) and subsequently by reacting a commercially available rhodium-olefin complex with an optically active bisphosphine denoted by L in an organic solvent such as methanol, ethanol, isopropanol, butanol, toluene, or tetrahydrofuran (accordingly, compounds (A) and (B) in the scheme 3 can be obtained), and optionally by further eliminating the olefin ligand by reacting the obtained compound with hydrogen gas (accordingly, a compound (C) in the scheme 3 can be obtained). Alternatively, the compound represented by the general formula (6) can be obtained by reaction of rhodium-olefin complex with 2 equivalent optically active bisphosphine denoted by the above L in an organic solvent such as methanol, ethanol, isopropanol, butanol, toluene, or tetrahydrofuran, and by successive counter-anion-exchange reaction with MX (M is a monovalent metal cation; and X is the same as described above) (accordingly, a compound (B) in the scheme 3 can be obtained) The COD in the chemical formula is 1,5-cyclooctadiene (the same shall apply hereinafter).

SCHEME 3

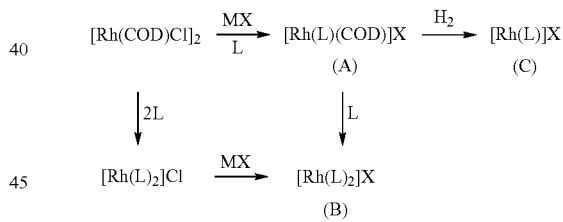

As shown in the following scheme 4, the compound represented by the general formula (6) used in the invention can be obtained also by reacting a rhodium-bisolefin complex previously subjected to counter-anion exchange reaction with an optically active bisphosphine denoted by L and optionally by further eliminating the olefin ligand with hydrogen gas.

SCHEME 4

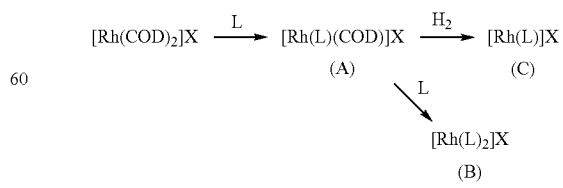

The amount of the optically active bisphosphine denoted by L to be added per mole of the center metal of the rhodium-olefin complex shown in the scheme 3 or the scheme 4 is preferably 1.0 to 2.4-fold moles, more preferably 1.05 to 2.2-fold moles since some part of the bisphosphine may be oxidized.

In the present invention, the rhodium-olefin complex used for producing the compound represented by the general formula (6) as the catalyst may be any of various complexes depending on the selected olefin ligand. However, for reasons of availability, a rhodium complex of 1,5-cyclooctadiene [Rh(COD)Cl]$_2$ and a rhodium complex of norbornadiene [Rh(NBD)Cl]$_2$ are particularly preferable. In the chemical formula, NBD is 2,5-norbornadiene (the same shall apply hereinafter).

In the counter-anion-exchange reaction, for example, silver salt (AgX) is preferably used as MX in terms of the handling easiness.

The catalytic active species in the compound represented by the general formula (6) is [Rh(L)$_m$]X. However, a precursor thereof, for example, the compound (A): [Rh(L)(COD)]X in the above-mentioned scheme, may also be used in the production method of the invention.

The compounds represented by the general formula (6) such as compounds (A), (B), and (C) in the above-mentioned scheme can be used for the production method of the invention without further purification after being prepared as a catalyst. Furthermore, in the production method of the invention, the catalyst containing rhodium metal and an optically active bisphosphine can be used immediately after the preparation thereof. Specifically, a rhodium compound and an optically active bisphosphine are reacted to prepare the catalyst, and subsequently a reactive substrate may be added.

The reaction solvent used in the production method of the invention is not particularly limited as long as it does not cause any adverse effect on the reaction, and examples of the solvent may include amides such as N,N-dimethylformamide, formamide, and N,N-dimethylacetamide; halohydrocarbons such as dichloromethane, 1,2-dichloroethane, chloroform, carbon tetrachloride, and o-dichlorobenzene; aliphatic hydrocarbons such as pentane, hexane, heptane, octane, decane, and cyclohexane; aromatic hydrocarbons such as benzene, toluene, and xylene; non-nucleophilic alcohols such as tert-butanol; ethers such as diethyl ether, diisopropyl ether, tert-butyl methyl ether, dimethoxyethane, ethylene glycol diethyl ether, tetrahydrofuran, 1,4-dioxane, and 1,3-dioxolane; and sulfoxides such as dimethyl sulfoxide. These reaction solvents may be used alone or in a suitable combination of two or more thereof.

In the production method of the invention, typically, the usage of 0.01 to 20 mol %, preferably 0.1 to 10 mol %, more preferably about 1 to 5 mol % of the catalyst containing rhodium metal and an optically active bisphosphine in terms of rhodium metal, to one of the reaction substrates, is typically sufficient.

In the production method of the invention, the reaction temperature for a [2+2+2] cycloaddition differs in accordance with the substrate used. However it is typically −20° C. to 100° C. and preferably in a range of 0° C. to 50° C. The reaction time naturally differs in accordance with the substrate used. However, it is typically 30 minutes to 30 hours and preferably 1 hour to 20 hours. The reaction is preferably carried out in an inert gas such as nitrogen or argon.

On completion of the reaction, post-treatment which is routinely carried out in this kind of field such as filtration, silica gel column chromatography, or the like is carried out, and purification such as crystallization, distillation, and various kinds of chromatography may be carried out alone or in combination to obtain an aimed optically active ester compound.

EXAMPLES

Hereinafter, the invention will be more specifically described by referring to the examples below. However, the invention is not limited to the illustrated examples.

The structural formulas of BINAPs, H$_8$-BINAP and SEGPHOS are shown below, and, in Examples, the notations of (R) or (S) with a ligand represent each absolute configuration of them.

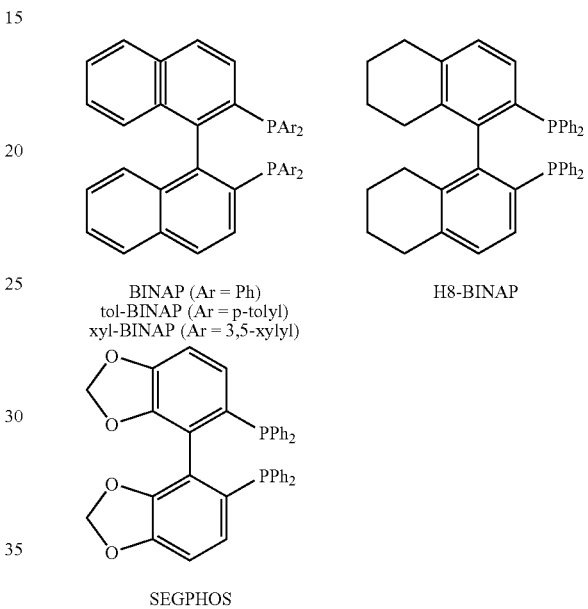

BINAP (Ar = Ph)
tol-BINAP (Ar = p-tolyl)
xyl-BINAP (Ar = 3,5-xylyl)

H8-BINAP

SEGPHOS

Example 1

Preparation of Optically Active Biaryl Diester

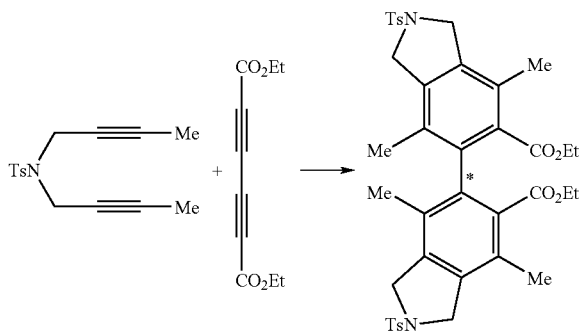

(Me, Et, and Ts in the scheme are a methyl, ethyl and tosyl group respectively. * is axial asymmetry.)

According to the above reaction scheme, optically active biaryl diester was produced.

Under an argon atmosphere, (R)-SEGPHOS (6.2 mg, 0.010 mmol), [Rh(COD)$_2$]BF$_4$ (4.1 mg, 0.010 mmol), and 1.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.4 mL of methylene chloride was added thereto. To the mixture, a solution of diethyl 2,4-hexadiyne-1,6-dicarboxylate (38.8 mg, 0.200 mmol) shown in the above reaction scheme in 0.4 mL of methylene chloride was added, and then a solution of N,N-bis(2-butynyl)tosylamide (165.2 mg, 0.600 mmol) in 1.2 mL of methylene chloride was added dropwise over 20 minutes. Then, the mixture was stirred at room temperature for 3 hour. Concentration of the reaction mixture and subsequent purification by thin-layer chromatography (ethyl acetate/triethylamine=20/1) gave the target material as a colorless solid in a yield of 54% with the optical purity of 98% ee.

m.p. 106.8-107.6° C.; $[\alpha]^{25}_D$ –5.86° (c 2.93, CHCl$_3$, >98% ee); IR (neat): 2980, 1721, 1163, 1347, 754 cm-$^1$; $^1$H NMR (CDCl$_3$, 300 MHz): δ 7.80 (d, J=8.1 Hz, 4H), 7.35 (d, J=8.1 Hz, 4H), 4.61 (s, 4H), 4.59 (s, 4H), 4.00-3.80 (m, 4H), 2.43 (s, 6H), 2.14 (s, 6H), 1.73 (s, 6H), 0.87 (t, J=6.9 Hz, 6H); $^{13}$C NMR (CDCl$_3$, 75 MHz) δ 167.9, 143.7, 136.2, 136.0, 135.0, 133.8, 133.7, 129.9, 129.6, 127.5, 127.2, 60.5, 53.7, 53.6, 21.5, 16.3, 16.1, 13.4; HRMS (ESI): calcd for C$_{40}$H$_{44}$N$_2$O$_8$S$_2$Na [M+Na]$^+$ 767.2437, found 767.2436; CHIRALPAK IA, hexane//CH$_2$Cl$_2$/2-PrOH=10:1:1, 1.0 mL/min, retention times: 34.2 min (major isomer) and 50.0 min (minor isomer).

Example 2

Preparation of Optically Active Biaryl Diester

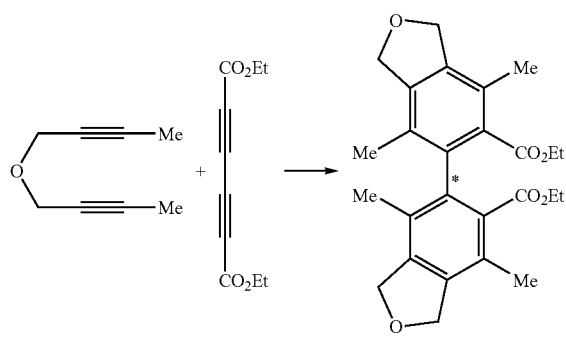

(Me and Et in the scheme are a methyl and ethyl group respectively. * is axial asymmetry.)

According to the above reaction scheme, optically active biaryl diester was produced.

Under an argon atmosphere, (R)-SEGPHOS (12.4 mg, 0.020 mmol), [Rh(COD)$_2$]BF$_4$ (8.2 mg, 0.020 mmol), and 2.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.8 mL of methylene chloride was added thereto. To the mixture, a solution of diethyl 2,4-hexadiyne-1,6-dicarboxylate (38.8 mg, 0.200 mmol) shown in the above reaction scheme in 0.4 mL of methylene chloride was added, and then a solution of 5-oxa-2,7-nonadiyne (244.34 mg, 2.00 mmol) in 3.0 mL of methylene chloride was added dropwise over 20 minutes. Then, the mixture was stirred at room temperature for 3 hour. Concentration of the reaction mixture and subsequent purification by thin-layer chromatography (ethyl acetate/triethylamine=20/1) gave the target material as a yellow solid in a yield of 28% with the optical purity of 99% ee.

Example 3

Preparation of Optically Active Biaryl Monoester

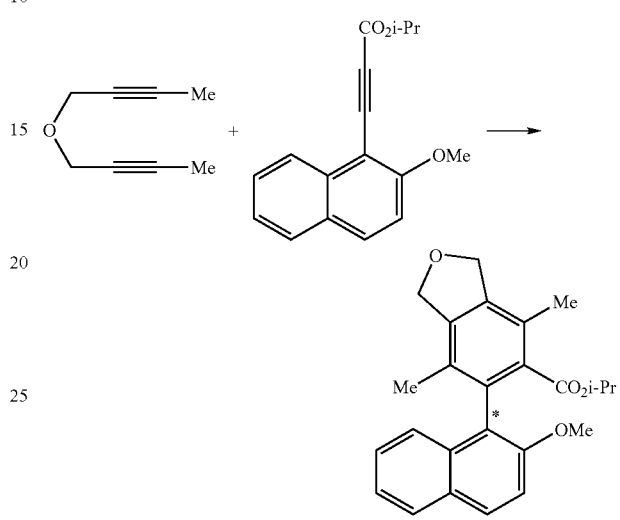

(Me and i-Pr in the scheme are a methyl and isopropyl group respectively. * is axial asymmetry.)

According to the above reaction scheme, optically active biaryl monoester was produced.

Under an argon atmosphere, (S)-BINAP (6.2 mg, 0.010 mmol), [Rh(COD)$_2$]BF$_4$ (4.1 mg, 0.010 mmol), and 2.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.4 mL of methylene chloride was added thereto. To the mixture, a solution of the monoyne compound (53.7 mg, 0.200 mmol) shown in the above reaction scheme in 0.4 mL of methylene chloride was added, and then a solution of the diyne compound (29.3 mg, 0.240 mmol) in 1.2 mL of methylene chloride was added dropwise over 20 minutes. Then, the mixture was stirred at room temperature for 1 hour. Concentration of the reaction mixture and subsequent purification by thin-layer chromatography (ethyl acetate/triethylamine=20/1) gave the target material as a yellow solid in a yield of 99% with the optical purity of 96% ee.

m.p. 35.4-36.6° C.; $[\alpha]^{25}_D$ +50.8° (c 3.76, CHCl$_3$, 96% ee); IR (KBr) 2978, 1720, 1594, 1466, 1264, 812 cm-$^1$; $^1$H NMR (CDCl$_3$, 300 MHz) δ 7.87 (d, J=9.0 Hz, 1H), 7.80-7.73 (m, 1H), 7.36-7.27 (m, 3H), 7.25-7.17 (m, 1H), 5.26-5.16 (m, 4H), 4.59 (sept, J=6.3 Hz, 1H), 3.86 (s, 3H), 2.25 (s, 3H), 1.78 (s, 3H), 0.69 (d, J =6.3 Hz, 3H), 0.42 (d, J=6.3 Hz, 3H); $^{13}$C NMR (CDCl$_3$, 75 MHz) δ 168.4, 154.2, 139.0, 137.7, 135.2, 133.5, 133.3, 129.4, 128.7, 128.5, 127.5, 126.3, 125.5, 125.2, 123.4, 121.3, 113,1, 74.1, 74.0, 67.6, 56.5, 21.0, 20.5, 16.3, 15.9; HRMS (ESI) calcd for C$_{25}$H$_{26}$O$_4$Na [M+Na]$^+$ 413.1723, found 413.1731; CHIRALPAK IC, hexane/THF=95:5, 0.5 mL/min, retention times: 22.2 min (minor isomer) and 24.9 min (major isomer).

Example 4-13

Preparation of Optically Active Biaryl Monoester

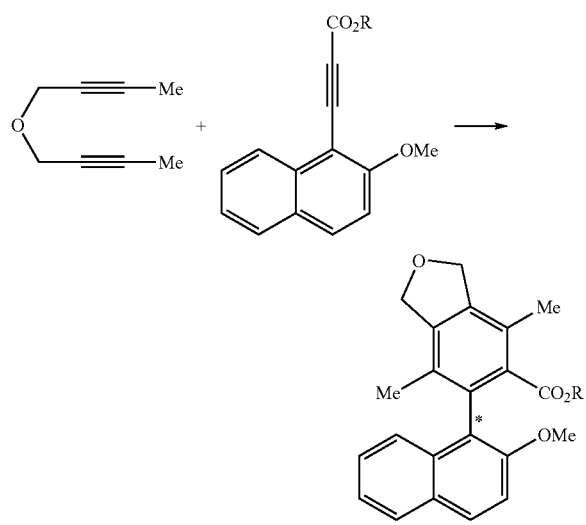

(Me in the scheme is a methyl group. * is axial asymmetry.)

The results obtained according to the method of Example 3 with using various bisphosphines or monoyne compounds are shown in Table 1 below.

TABLE 1

| No. | R | bisphosphine | Cat. Ratio | Time (hr) | yield (%) | Optical purity |
|---|---|---|---|---|---|---|
| 4 | Me | (S)-H8-BINAP | 5 mol % | 1 | 84 | 89% ee |
| 5 | Me | (S)-BINAP | 10 mol % | 1 | 88 | 91% ee |
| 6 | Et | (R)-H8-BINAP | 10 mol % | 17 | >90 | 94% ee |
| 7 | Et | (S)-BINAP | 10 mol % | 1 | 99 | 94% ee |
| 8 | Et | (S)-SEGPHOS | 10 mol % | 17 | 82 | 86% ee |
| 9 | i-Pr | (S)-H8-BINAP | 10 mol % | 1 | 97 | 94% ee |
| 10 | i-Pr | (S)-SEGPHOS | 10 mol % | 1 | 97 | 88% ee |
| 11 | i-Pr | (S)-BINAP | 10 mol % | 1 | >99 | 96% ee |
| 12 | i-Pr | (S)-tol-BINAP | 10 mol % | 1 | 99 | 96% ee |
| 13 | i-Pr | (S)-xyl-BINAP | 10 mol % | 1 | 99 | 91% ee |

"Cat. Ratio" represent ratio of catalyst to monoyne.

Example 14-21

Preparation of Optically Active Biaryl Monoester

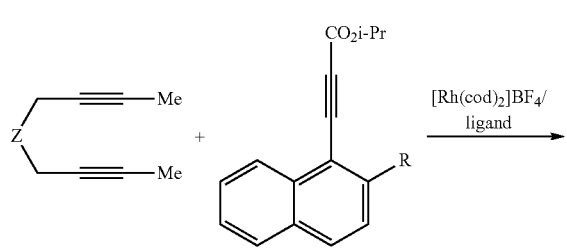

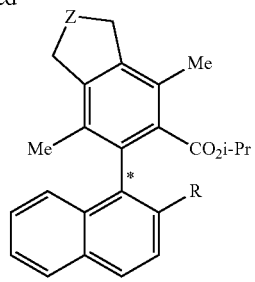

(Me and i-Pr in the scheme are a methyl and isopropyl group respectively. * is axial asymmetry.)

According to the above reaction scheme, optically active biaryl monoester was produced.

Under an argon atmosphere, ligand (0.010 mmol), [Rh (COD)$_2$]BF$_4$ (4.1 mg, 0.010 mmol), and 2.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.4 mL of methylene chloride was added thereto. To the mixture, a solution of the monoyne compound (0.200 mmol) shown in the above reaction scheme in 0.4 mL of methylene chloride was added, and then a solution of the diyne compound (0.220 mmol) in 1.2 mL of methylene chloride was added dropwise over 20 minutes. Then, the mixture was stirred at room temperature for 1 hour. Concentration of the reaction mixture and subsequent purification by thin-layer chromatography (ethyl acetate/triethylamine=20/1) gave the target compound. The results are shown in Table 2 below.

TABLE 2

| No. | Z | R | ligand | yield (%) | Optical purity |
|---|---|---|---|---|---|
| 14 | O | OMe | (S)-BINAP | >99 | 96% ee |
| 15 | O | OMe | (R)-BINAP | 97 | 95% ee |
| 16 | NTs | OMe | (S)-BINAP | >99 | 90% ee |
| 17 | CH$_2$ | OMe | (S)-BINAP | 93 | 97% ee |
| 18 | CH$_2$CH$_2$ | OMe | (S)-BIANP | 71 | 93% ee |
| 19 | O | OCH$_2$OMe | (S)-BINAP | 95 | 91% ee |
| 20 | O | OBn | (S)-BINAP | 91 | 89% ee |

Example 21

Preparation of Optically Active Biaryl Monoester

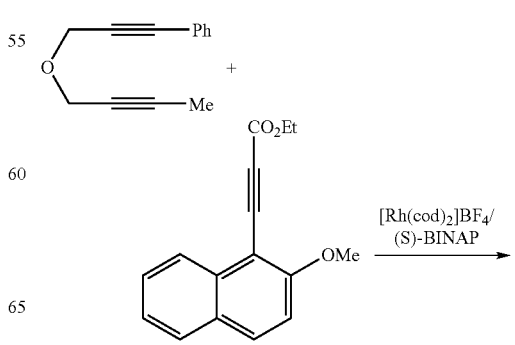

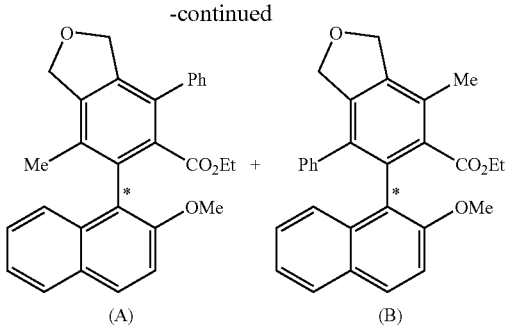

(A) (B)

(Me, Et, and Ph in the scheme are a methyl, ethyl and phenyl group respectively. * is axial asymmetry.)

According to the above reaction scheme, optically active biaryl monoester was produced.

Under an argon atmosphere, (S)-BINAP (6.3 mg, 0.010 mmol), [Rh(COD)$_2$]BF$_4$ (4.1 mg, 0.010 mmol), and 2.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.8 mL of methylene chloride was added thereto. To the mixture, a solution of the monoyne compound (50.9 mg, 0.200 mmol) and diyne compound (44.2 mg, 0.240 mmol) shown in the above reaction scheme in 3.2 mL of methylene chloride was added dropwise. Then, the mixture was stirred at room temperature for 3 hours. Concentration of the reaction mixture and subsequent purification by thin-layer chromatography (toluene/ethyl acetate/triethylamine=25/1/1) gave the mixture of compound (A) and (B) ((A)/(B)=94/6) in a yield of 99%. The optical purity of compound (A) and (B) were 74% ee and 62% ee, respectively.

Examples 22

Preparation of Optically Active Biaryl Diester

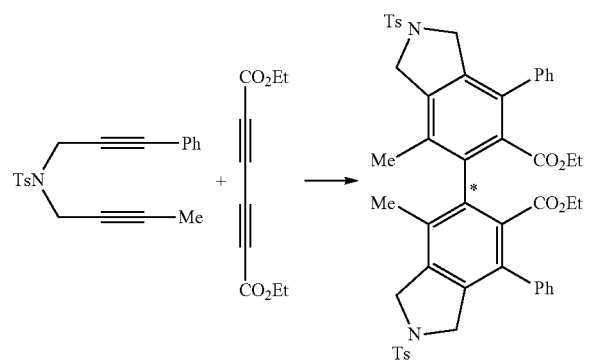

(Me, Et, Ts, and Ph in the scheme are a methyl, ethyl, tosyl and phenyl group respectively. * is axial asymmetry.)

According to the above reaction scheme, optically active biaryl diester was produced.

Under an argon atmosphere, (R)—H8-BINAP (6.3 mg, 0.010 mmol), [Rh(COD)$_2$]BF$_4$ (4.1 mg, 0.010 mmol), and 1.0 mL of methylene chloride were placed into a schlenk tube, and stirred for 5 minutes. Then, hydrogen gas was introduced into the schlenk tube, and the mixture was stirred for 1 hour. Successively, the reaction mixture was concentrated to dryness in vacuo, and 0.4 mL of methylene chloride was added thereto. To the mixture, a solution of diethyl 2,4-hexadiyne-1,6-dicarboxylate (38.8 mg, 0.200 mmol) shown in the above reaction scheme in 0.4 mL of methylene chloride was added, and then a solution of N-(2-butynyl)-N-(3-phenyl-2-propynyl)tosylamide (0.600 mmol) in 1.2 mL of methylene chloride was added dropwise over 20 minutes. Then, the mixture was stirred at room temperature for 3 hours. Concentration of the reaction mixture and subsequent purification by thin-layer chromatography (ethyl acetate/triethylamine=20/1) gave the target material as a colorless solid in a yield of 50% with the optical purity of 88% ee.

$^1$H NMR (CDCl$_3$, 300 MHz) δ 7.74 (d, J=8.1 Hz, 4H), 7.39-7.28 (m, 10H), 7.17-7.08 (m, 4H), 4.65 (s, 4H), 4.54 (d, J=13.8 Hz, 2H), 4.39 (d, J=14.1 Hz, 2H), 3.61 (dq, J=10.8, 7.2 Hz, 2H), 3.54 (dq, J=10.8, 7.2 Hz, 2H), 2.43 (s, 6H), 1.89 (s, 6H), 0.56 (t, J=7.2 Hz, 6H).

CHIRALPAK IA, hexane/CH$_2$Cl$_2$=3:1, 0.8 mL/min, retention times: 40.6 min (major isomer) and 49.4 min (minor isomer).

The analysis data of the resulting compounds, and the structural formulas identified thereby, are shown below:

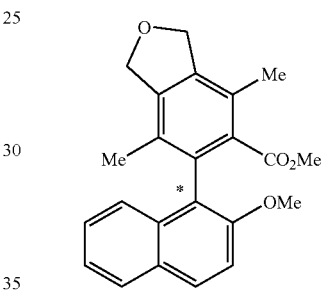

Colorless solid; m.p. 148.3-149.2° C.; [α]$^{25}_D$-42.8° (c 2.70, CHCl$_3$, 91% ee); IR (KBr) 2947, 1722, 1593, 1430, 1264, 813 cm$^{-1}$; $^1$H NMR (CDCl$_3$, 300 MHz) δ 7.87 (d, J=9.0 Hz, 1H), 7.82-7.74 (m, 1H), 7.39-7.26 (m, 3H), 7.25-7.15 (m, 1H), 5.21 (s, 4H), 3.86 (s, 3H), 3.15 (s, 3H), 2.24 (s, 3H), 1.78 (s, 3H); $^{13}$C NMR (CDCl$_3$, 75 MHz) δ 169.5, 154.1, 139.3, 137.7, 134.7, 133.7, 133.2, 129.5, 128.7, 127.7, 126.4, 125.8, 124.9, 123.5, 121.3, 113.1, 74.1, 74.0, 56.6, 51.2, 16.5, 16.0; HRMS (ESI) calcd for C$_{23}$H$_{22}$O$_4$Na [M+Na]$^+$ 385.1410, found 385.1435; CHIRALPAK IC, hexane/CH$_2$Cl$_2$/2-PrOH=360:40:3, 0.7 mL/min, retention times: 29.2 min (major isomer) and 41.3 min (minor isomer).

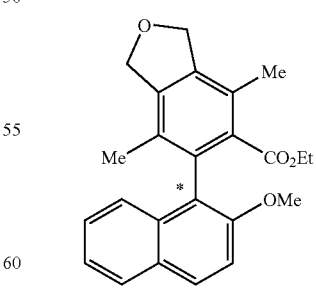

Colorless solid; m.p. 106.1-107.7° C.; [α]$^{25}_D$+44.3° (c 3.13, CHCl$_3$, 94% ee); IR (KBr) 2938, 1725, 1593, 1473, 1266, 807 cm$^{-1}$; $^1$H NMR (CDCl$_3$, 300 MHz) δ 7.87 (d, J=9.0 Hz, 1H), 7.82-7.73 (m, 1H), 7.36-7.19 (m, 4H), 5.21 (s, 4H), 3.86 (s, 3H), 3.67 (dq, J=14.4, 7.2 Hz, 1H), 3,63 (dq, J=14.4, 7.2 Hz, 1H), 2.25 (s, 3H), 1.78 (s, 3H), 0.45 (t, J=7.2 Hz, 3H); $^{13}$C NMR (CDCl$_3$, 75 MHz) δ 168.9, 154.2, 139.1, 137.7, 134.9, 133.5, 133.4, 129.4, 128.7, 128.6, 127.6, 126.3, 125.7, 125.0, 123.4, 121.3, 113,1, 74.1, 74.0, 60.1, 56.5, 16.4, 16.0, 13.0; HRMS (ESI) calcd for C$_{24}$H$_{24}$O$_4$Na [M+Na]$^+$ 399.1567, found 399.1589; CHIRALPAK IC, hexane/THF=95:5, 0.5 mL/min, retention times: 25.2 min (minor isomer) and 27.2 min (major isomer).

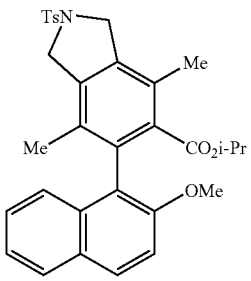

Colorless solid; m.p. 73.6-74.8° C.; [α]$^{25}_D$+12.2° (c 2.73, CHCl$_3$, 90% ee); IR (KBr) 2978, 1720, 1595, 1457, 1347, 1265, 667 cm$^{-1}$; $^1$H NMR (CDCl$_3$, 300 MHz) δ 7.91-7.80 (m, 3H), 7.80-7.73 (m, 1H), 7.41-7.33 (m, 2H), 7.33-7.24 (m, 3H), 7.14-7.07 (m, 1H), 4.78-4.59 (m, 4H), 4.55 (sept, J=6.3 Hz, 1H), 3.82 (s, 3H), 2.45 (s, 3H), 2.20 (s, 3H), 1.74 (s, 3H), 0.67 (d, J=6.3 Hz, 3H), 0.38 (d, J=6.3 Hz, 3H); $^{13}$C NMR (CDCl$_3$, 75 MHz) δ 168.0, 154.2, 143.7, 136.1, 135.7, 134.8, 133.8, 133.7, 133.3, 130.0, 129.9, 129.6, 128.7, 127.6, 127.5, 126.7, 126.4, 125.0, 123.5, 120.8, 113.0, 67.8, 56.5, 54.0, 53.8, 21.5, 21.0, 20.4, 16.1, 15.8; HRMS (ESI) calcd for C$_{32}$H$_{33}$NO$_5$SNa [M+Na]$^+$ 566.1972, found 566.1977; CHIRALPAK AD-H, hexane/2-PrOH=90:10, 1.0 mL/min, retention times: 22.1 min (major isomer) and 27.9 min (minor isomer).

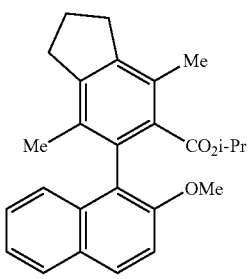

Pale yellow oil; [α]$^{25}_D$+53.4° (c 3.55, CHCl$_3$, 97% ee); IR (neat) 2935, 1719, 1594, 1464, 1262, 810 cm$^{-1}$; $^1$H NMR (CDCl$_3$, 300 MHz) δ 7.83 (d, J=9.0 Hz, 1H), 7.78-7.69 (m, 1H), 7.35-7.18 (m, 4H), 4.56 (sept, J=6.3 Hz, 1H), 3.85 (s, 3H), 2.96 (t, J=7.5 Hz, 2H), 2.94 (t, J=7.5 Hz, 2H), 2.27 (s, 3H), 2.14 (quint, J=7.5 Hz, 2H), 1.80 (s, 3H), 0.68 (d, J=6.3 Hz, 3H), 0.40 (d, J=6.3 Hz, 3H); $^{13}$C NMR (CDCl$_3$, 75 MHz) δ 169.2, 154.3, 143.9, 142.5, 133.81, 133.76, 131.4, 130.7, 129.0, 128.7, 127.4, 126.0, 125.6, 123.3, 122.5, 113.3, 67.2, 56.5, 32.5, 32.2, 24.1, 21.1, 20.5, 16.6, 16.2; HRMS (ESI) calcd for C$_{26}$H$_{28}$O$_3$Na [M+Na]$^+$ 411.1931, found 411.1936; doubly connected CHIRALPAK AD-H, hexane/2-PrOH=97:3, 0.5 mL/min, retention times: 23.4 min (major isomer) and 27.1 min (minor isomer).

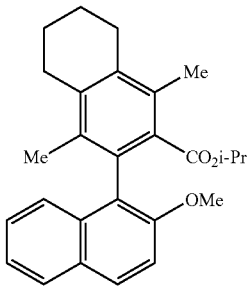

Colorless solid; m.p. 38.9-40.3 ° C.; [α]$^{25}_D$+44.7° (c 0.62, CHCl$_3$, 93% ee); IR (KBr) 2932, 1720, 1594, 1464, 1263, 809 cm$^{-1}$; $^1$H NMR (CDCl$_3$, 300 MHz) δ 7.84 (d, J=9.0 Hz, 1H), 7.80-7.72 (m, 1H), 7.35-7.19 (m, 4H), 4.54 (sept, J=6.3 Hz, 1H), 3.86 (s, 3H), 2.85-2.62 (m, 4H), 2.21 (s, 3H), 1.85 (quint, J=3.3 Hz, 4H), 1.78 (s, 3H), 0.72 (d, J=6.3 Hz, 3H), 0.36 (d, J=6.3 Hz, 3H); $^{13}$C NMR (CDCl$_3$, 75 MHz) δ 169.5, 154.4, 136.7, 135.3, 133.9, 133.6, 133.5, 129.8, 129.6, 129.1, 128.8, 127.4, 126.1, 125.8, 123.3, 122.8, 113.3, 67.3, 56.6, 28.1, 27.7, 22.92, 22.86, 21.2, 20.5, 16.3, 15.7; HRMS (ESI) calcd for C$_{27}$H$_{30}$O$_3$Na [M+Na]$^+$ 425.2087, found 425.2109; SUMICHIRAL OA-3100, hexane/2-PrOH=95:5, 0.5 mL/min, retention times: 15.2 min (minor isomer) and 18.5 min (major isomer).

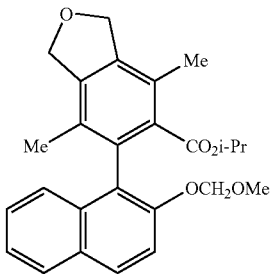

Colorless oil; [α]$^{25}_D$+61.7° (c 2.75, CHCl$_3$, 91% ee); IR (neat) 2978, 1719, 1594, 1470, 1240, 1014 cm$^{-1}$; $^1$H NMR (CDCl$_3$, 300 MHz) δ 7.83 (d, J=9.0 Hz, 1H), 7.81-7.74 (m, 1H), 7.52 (d, J=9.0 Hz, 1H), 7.36-7.28 (m, 2H), 7.25-7.20 (m, 1H), 5.26-5.17 (m, 4H), 5.21 (d, J=7.2 Hz, 1H), 5.11 (d, J=7.2 Hz, 1H), 4.59 (sept, J=6.3 Hz, 1H), 3.42 (s, 3H), 2.25 (s, 3H), 1.79 (s, 3H), 0.70 (d, J=6.3 Hz, 3H), 0.34 (d, J=6.3 Hz, 3H); $^{13}$C NMR (CDCl$_3$, 75 MHz) δ 168.4, 152.3, 139.0, 137.7, 135.2, 133.6, 133.3, 129.4, 128.5, 127.5, 126.19, 126.18, 125.51, 125.49, 123.8, 122.5, 116.3, 95.0, 74.1, 74.0, 67.7, 55.9, 21.0, 20.4, 16.3, 16.0; HRMS (ESI) calcd for C$_{26}$H$_{28}$O$_5$Na [M+Na]$^+$ 443.1829, found 443.1857; doubly connected CHIRALPAK AD-H, hexane/2-PrOH=97:3, 0.5 mL/min, retention times: 35.7 min (major isomer) and 38.9 min (minor isomer).

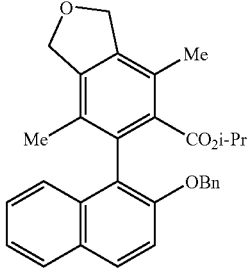

Colorless solid; m.p. 31.8-32.9° C.; [α]$^{25}_D$+33.4° (c 3.69, CHCl$_3$, 89% ee); IR (KBr) 2978, 1720, 1593, 1454, 1262, 747 cm$^{-1}$; $^1$H NMR (CDCl$_3$, 300 MHz) δ 7.79 (d, J=9.0 Hz, 1H), 7.77-7.70 (m, 1H), 7.35-7.19 (m, 9H), 5.26-5.16 (m, 4H), 5.16 (s, 2H), 4.61 (sept, J=6.3 Hz, 1H), 2.27 (s, 3H), 1.76 (s, 3H), 0.70 (d, J=6.3 Hz, 3H), 0.36 (d, J=6.3 Hz, 3H); $^{13}$C NMR (CDCl$_3$, 75 MHz) δ 168.5, 153.6, 139.0, 137.9, 137.6, 135.2, 133.6, 133.4, 129.3, 129.0, 128.6, 128.2, 127.5, 127.4, 126.6, 126.2, 125.5, 125.5, 123.6, 122.5, 115.3, 74.1, 74.0, 71.2, 67.6, 21.1, 20.4, 16.4, 16.1; HRMS (ESI) calcd for C$_{31}$H$_{30}$O$_4$Na [M+Na]$^+$ 489.2036, found 489.2049; CHIRALPAK AD-H, hexane/2-PrOH=95:5, 0.5 mL/min, retention times: 18.2 min (major isomer) and 21.2 min (minor isomer).

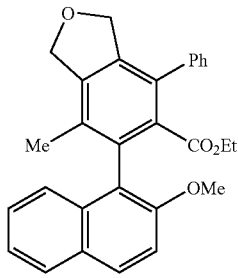

Colorless solid; m.p. 57.9-58.7° C.; IR (KBr) 1727, 1267, 1187, 1033, 705 cm$^{-1}$; $^1$H NMR (CDCl$_3$, 300 MHz) major product: δ 7.88 (d, J=9.3 Hz, 1H), 7.79 (d, J=8.1 Hz, 1H), 7.46-7.25 (m, 9H), 5.25 (s, 2H), 5.16 (d, J=12.6 Hz, 1H), 5.10 (d, J=12.6 Hz, 1H), 3.89 (s, 3H), 3,39 (q, J=7.2 Hz, 2H), 1.85 (s, 3H), 0.32 (t, J=7.2 Hz, 3H); methyl protons of OEt, OMe, and Ar—Me for minor product: δ 3.70 (s, 3H), 2.33 (s, 3H), 0.45 (t, J=7.2 Hz, 3H); $^{13}$C NMR (CDCl$_3$, 75 MHz) δ 168.3, 154.3, 139.6, 139.2, 138.42, 138.37, 137.2, 134.9, 134.0, 133.4, 131.3, 130.4, 129.6, 129.4, 128.7, 128.4, 128.2, 128.0, 127.6, 127.4, 127.2, 126.4, 125.1, 123.4, 121.0, 113.3, 74.2, 74.0, 73.9, 60.0, 56.6, 56.1, 16.2, 12.9; HRMS (ESI) calcd for C$_{29}$H$_{26}$O$_4$Na [M+Na]$^+$ 461.1723, found 461.1728; CHIRALPAK AD-H, hexane/2-PrOH=97:3, 0.5 mL/min, retention times for major product: 27.4 min (minor isomer) and 35.8 min (major isomer); retention times for minor product: 20.7 min (minor isomer) and 41.3 min (major isomer).

The invention claimed is:

1. An optically active compound represented by the following general formula (4'):

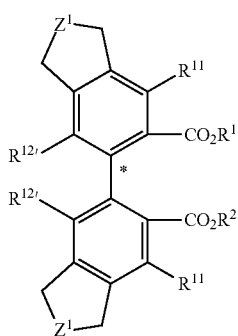

wherein, R$^1$ and R$^2$ may be the same or different and are hydrogen atom, an alkali metal, or an alkyl group optionally having a substituent selected from the group consisting of alkoxy groups and halogen atoms; R$^{11}$ is hydrogen atom, an alkyl group optionally having a substituent selected from the group consisting of alkoxy groups and halogen atoms, a cycloalkyl group optionally having a substituent selected from the group consisting of alkoxy groups and halogen atoms, or an aryl group optionally having a substituent selected from the group consisting of linear or branched alkyl groups having 1 to 6 carbon atoms, linear or branched alkoxy groups having 1 to 6 carbon atoms and halogen atoms; R$^{12'}$ is an alkyl group optionally having a substituent selected from the group consisting of alkoxy groups and halogen atoms, a cycloalkyl group optionally having a substituent selected from the group consisting of alkoxy groups and halogen atoms, or an aryl group optionally having a substituent selected from the group consisting of linear or branched alkyl groups having 1 to 6 carbon atoms, linear or branched alkoxy groups having 1 to 6 carbon atoms and halogen atoms; Z$^1$ is an oxygen, a sulfur atom, a methylene chain, NR$^N$ (wherein R$^N$ is alkyl, aryl, alkanesulfonyl, arylsulfonyl, or acyl group) or Si(R$^{Si}$)$_2$ (wherein R$^{Si}$ is an alkyl or aryl group or may form a ring as Si(R$^{Si}$)$_2$; two R$^{12'}$ may form a ring optionally having a substituent selected from the group consisting alkyl groups, alkoxy groups and halogen atoms, or a methylene chain optionally having a substituent selected from the group consisting of alkyl groups having 1 to 4 carbon atoms, alkoxy groups having 1 to 4 carbon atoms, alkoxycarbonyl groups having an alkoxy group having 1 to 4 carbon atoms and halogen atoms and optionally having oxygen atom or sulfur atom in the chain, in combination with each other; and * is axial asymmetry.

2. An optically active compound represented by the following general formula (8'):

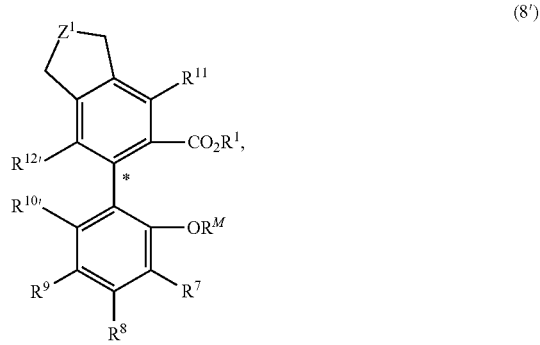

wherein, R$^1$ is hydrogen atom, alkali metal, or an alkyl group optionally having a substituent selected from the group consisting of alkoxy groups and halogen atoms; R$^M$ is hydrogen atom or a protecting group of hydroxyl group; R$^7$, R$^8$ and R$^9$ are independently hydrogen atom, an alkyl group optionally having a substituent selected from the group consisting of alkoxy groups and halogen atoms, a cycloalkyl group optionally having a substituent selected from the group consisting of alkoxy groups and halogen atoms, an aryl group optionally having a substituent selected from the group consisting of linear or branched alkyl groups having 1 to 6 carbon atoms, linear or branched alkoxy groups having 1 to 6 carbon atoms and halogen atoms, an alkoxy group optionally having a substituent selected from the group consisting of halogen atoms and aryl groups, or an aryloxy group optionally having a substituent selected from the group consisting of linear or branched alkyl groups having 1 to 6 carbon atoms, linear or branched alkoxy groups having 1 to 6 carbon atoms and halogen atoms; $R^{11}$ is a hydrogen atom, an alkyl group optionally having a substituent selected from the group consisting of alkoxy groups and halogen atoms, a cycloalkyl group optionally having a substituent selected from the group consisting of alkoxy groups and halogen atoms, or an aryl group optionally having a substituent selected from the group consisting of linear or branched alkyl groups having 1 to 6 carbon atoms, linear or branched alkoxy groups having 1 to 6 carbon atoms and halogen atoms; $R^{10'}$ and $R^{12'}$ are independently an alkyl group optionally having a substituent selected from the group consisting of alkoxy groups and halogen atoms, a cycloalkyl group optionally having a substituent selected from the group consisting of alkoxy groups and halogen atoms, or an aryl group optionally having a substituent selected from the group consisting of linear or branched alkyl groups having 1 to 6 carbon atoms, linear or branched alkoxy groups having 1 to 6 carbon atoms and halogen atoms; any two adjacent groups among $R^7$, $R^8$ and $R^9$ may form an aromatic ring optionally having a substituent selected from the group consisting of alkyl groups, alkoxy groups and halogen atoms, a methylene chain optionally having a substituent selected from the group consisting of alkyl groups having 1 to 4 carbon atoms, alkoxy groups having 1 to 4 carbon atoms, alkoxycarbonyl groups having an alkoxy group having 1 to 4 carbon atoms and halogen atoms, or a (poly)methylenedioxy group optionally having a substituent selected from the group consisting of alkyl groups having 1 to 4 carbon atoms, alkoxy groups having 1 to 4 carbon atoms, alkoxycarbonyl groups having an alkoxy group having 1 to 4 carbon atoms and halogen atoms; $Z^1$ is an oxygen, a sulfur atom, a methylene chain, $NR^N$ (wherein $R^N$ is alkyl, aryl, alkanesulfonyl, arylsulfonyl, or acyl group) or $Si(R^{Si})_2$ (wherein $R^{Si}$ is an alkyl or aryl group or may form a ring as $Si(R^{Si})_2$; and * is axial asymmetry.

* * * * *